United States Patent [19]
Carson

[11] Patent Number: 6,078,839
[45] Date of Patent: Jun. 20, 2000

[54] ABRASION RESISTANT IMPLANTABLE LEAD INSULATION PROTECTOR

[75] Inventor: Dean F. Carson, Mountain View, Calif.

[73] Assignee: Pacesetter, Inc., Sunnyvale, Calif.

[21] Appl. No.: 09/208,721

[22] Filed: Dec. 9, 1998

[51] Int. Cl.[7] .................................................. A61N 1/05
[52] U.S. Cl. ................................................................ 607/116
[58] Field of Search .................................. 607/116, 115, 607/122, 123

[56] References Cited

U.S. PATENT DOCUMENTS 5,683,446  11/1997  Gates ........................................ 607/116
5,843,149  12/1998  Ebert et al. .............................. 607/116

Primary Examiner—Scott M. Getzow
Attorney, Agent, or Firm—Steven M. Mitchell

[57] ABSTRACT

An abrasion resistant implantable lead is described including a protector for preventing abrasion to lead insulation. A helix-shaped protector can be placed around portions of the implantable lead to prevent frictional contact between the lead and the metallic casing of an implantable medical device, known as a pulse generator. The protector can have a cross-section and end-view of various shapes. The protector can be made of a flexible, elastomeric biocompatible material and can be coated by a hydrophilic surface to minimize the coefficient of friction between the protector and the casing of the pulse generator. The protector can have an inner cross-sectional diameter equal to or less than an outer cross-sectional diameter of the lead insulation, ensuring a snug fit. A toolkit for selecting, sizing and positioning the proper protector is described.

16 Claims, 7 Drawing Sheets

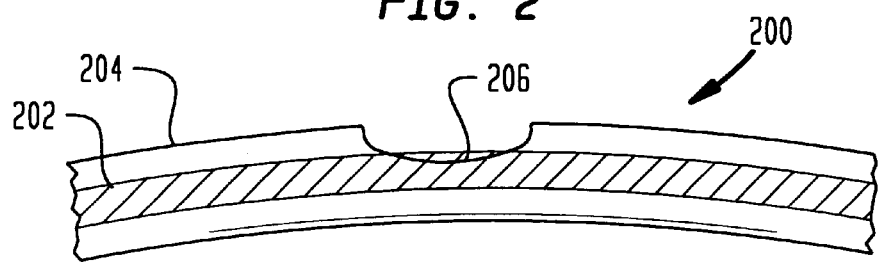
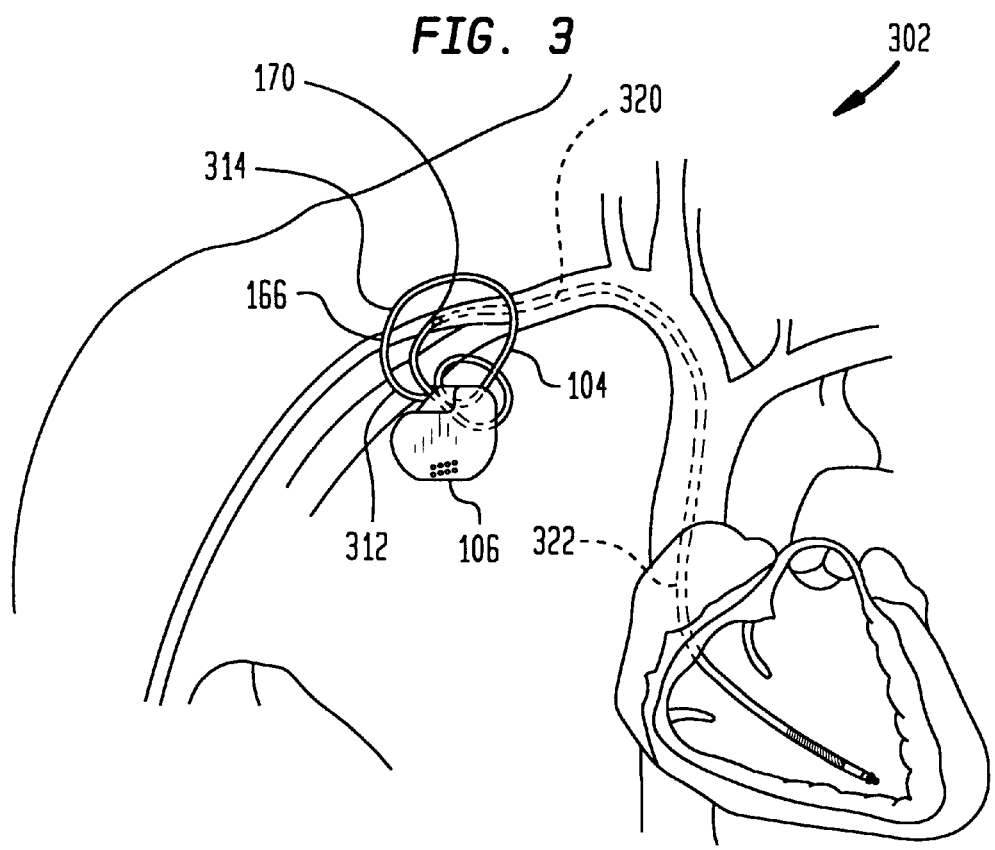

ABRASION RESISTANT IMPLANTABLE LEAD INSULATION PROTECTOR

BACKGROUND OF THE INVENTION

1. Field of the Invention

The present invention relates generally to implantable medical devices, and more particularly to implantable leads. Even more particularly, the invention relates to an abrasion and tear resistant implantable lead.

2. Related Art

Implantable leads deliver electrical therapy to a patient's heart. Such a lead is coupled at one end to an implantable medical device, such as, for example, an implantable cardioverter defibrillator (ICD) or a pacemaker. These devices are generally known as pulse generators.

The implantable lead when coupled to an ICD, delivers therapy in the form of an electrical current to the heart in an attempt to correct a detected cardiac arrhythmia. Heartbeat irregularities are fairly common and many are harmless. A severe heartbeat irregularity known as a ventricular tachycardia is an abnormally rapid heartbeat. An implantable lead and an ICD are designed to work together to apply such therapy automatically and quickly to minimize damage to the heart.

ICDs and pacemakers monitor and deliver pacing pulses to a patient's heartbeat through a pacing/sensing electrode of the lead and an ICD delivers high voltage electrical pulses through a defibrillation electrode of the lead. The housing of implantable medical device or pulse generator, such as an ICD or a pacemaker, is commonly referred to as a case or "can."

Implantable leads, whether epicardial or endocardial, are thus used to deliver electrical pulses from a pulse generator to a patient's heart. Such leads are coupled to one or more terminals on the pulse generator at one end, known as the proximal end, by connector pins on one or more legs of the lead. On the distal end of the lead, one or more electrodes are used to deliver electrical therapy to the patient's heart. In the case of a bifurcated or trifurcated lead, a yoke connects the legs to the lead body. The implantable lead includes one or more electrical conductors or wires extending along the length of the lead and electrically connecting the proximal lead connectors to the electrodes. The conductors of the lead are surrounded by a flexible, electrically resistant material such as silicone or polyurethane, referred to as insulation.

The lead is typically implanted through a vein (the cephalic and subclavian veins are the most common) near the patient's neck and threaded down to the heart. The proximal end of the lead is then tunneled under the facia to a pocket in the pectoral region created by an incision in the patient's chest. After testing of the leads to ensure proper placement, the pulse generator is then surgically implanted into the patient's chest, in the pocket.

Unfortunately, conventional implantable leads are susceptible to insulation defects and fractures from frictional contact between the lead and pulse generator or from contact between the leads. The exterior of the pulse generator is usually made from a metal, such as, for example, titanium. Movement of the titanium pulse generator against an implantable lead can abrade the lead's insulation, ultimately exposing conductors resulting in lead failure. Failure of a rate-sensing lead could cause, for example, a defibrillator to misidentify a patient's fibrillating heart (i.e., failure to sense), deliver inappropriate therapy (e.g., misidentify a normal sinus rhythm as fibrillation), or even cause ventricular fibrillation (VF).

Such lead failure is well documented. See DeLurgio D. B., Sorrentino D. M., Leon A. R., Langberg J. J., *Implanted Cardioverter Defibrillator (ICD) Lead Abrasion is a Universal Problem*, Emory University Hospital, Atlanta, Ga. Supplement I, Circulation Vol. 94, No. 8, p. 564, Oct. 15, 1996, and DeLurgio, D. B., Sathavorn C., Mera F., Leon A., Walter P. F., Langberg J. J., *Incidence and Implications of Abrasion of Implantable Cardioverter-Defibrillator Leads*, Emory University Hospital, Atlanta, Ga., Jan. 28, 1997, the contents of which are incorporated herein by reference in their entirety.

When a lead is transvenously implanted, the lead is sutured into place and the excess lead length can be wrapped in a loop and be placed adjacent to, e.g., behind and against, the pulse generator. Friction between the lead and the pulse generator's case can result in lead insulation defects, i.e. breaks in the insulation exposing one or more conductors. A short circuit can occur between the conductor at the site of the insulation defect and the electrically active case of the pulse generator resulting in a high current flow directed to a small area of the pulse generator. Thus, potential damage to the internal medical device circuitry can warrant generator replacement upon identification of lead defects. See Gummert J., Krauss B., Hutschenreiter W., Hambrecht R., Mohr F. W., *Sensing Lead Insulation Defect Resulting in a Damage of the ICD Pulse Generator Case*, Department of Cardiac Surgery, Department of Cardiology University Leipzig, Leipzig, Germany, Pace, Vol. 21, pp. 478 and 479, February, 1998, the contents of which is incorporated herein by reference in its entirety.

Inevitable, eventual, battery depletion requires removal and replacement of the pulse generator by surgery. For cosmetic reasons, to avoid multiple incision scars, it is preferable for pulse generator replacement that the prior incision be carefully reincised by the surgeon. Reincision however, requires that the surgeon take great care to protect the underlying leads. Unfortunately, reincision could result in inadvertent damage via scalpel nicks and cuts to the silicone insulation of the leads, requiring repair or replacement of the leads. When cutting away adhered tissue, scalpel nicks of silicone can propagate into full thickness tears. Lead inspection and replacement may at times be necessary. During routine device replacements due to battery depletion, as already discussed, or device upgrades, e.g., single to dual chamber and to smaller size pulse generators, the end of the lead which attaches to the pulse generator is exposed for examination of any abrasions caused by the pulse generator. If extensive lead abrasions are found, the lead must be extracted and replaced. Removal and replacement of a lead is both costly and potentially risky. Alternatively, the insulation of the lead could be patched by a messy and unreliable technique of manually patching the lead with room temperature vulcanization (RTV) biocompatible silicone material. Abandonment of leads is also widely practiced, but has drawbacks as well.

Currently no device-related preventative measures (such as reinforced silicone) to address lead abrasion are commercially available. Silicone has a superior thirty year reputation of reliability, but has relatively poor abrasion and tear resistance. Polyurethane is more resistant to cuts or tears, but historically has had biodegradation problems. Biodegradation properties of materials include environmental stress crack resistance (ESCR) and the propensity to exhibit metal ion oxidation (MIO). ESCR refers to the propensity of a polymer to resist degrading when stressed and also particularly when in a highly acid or oxidative environment. ESCR is a mechanism by which plastics fail by small cracking or crazing. MIO refers to a property of lead insulation material, by which ions have been implicated with inducing cracking in the insulation of the lead material, due to the conductors used in the lead.

What is needed then is an improved, tear and abrasion resistant silicone insulated lead.

SUMMARY OF THE INVENTION

The present invention is a tear and abrasion resistant device for use on an implantable lead having insulation, the device including a protector placed about a portion of the insulation, especially where lead/device contact and reincision cutdowns occur. The protector is configured to substantially prevent abrasion of the insulation by physically separating the insulation from contact with an implanted pulse generator. The protector is also configured to prevent tearing by placing a cut-resistant material over the insulation.

The protector of the present invention is made from a flexible, elastomeric, biocompatible material such as a thermoset or thermoplastic homopolymer, a blend of polymers, a coated polymer, or a filled polymer. Specific polymers include polytetrafluoroethylene (PTFE), polyurethanes, polycarbonate polyurethanes, polyolefins, polyesters, or other known polymers with an acceptable history of long-term implant use.

The protector can have a hydrophilic surface coating to minimize the coefficient of friction between the protector and the pulse generator. The surface coating can also include heparin or other antithrombogenic coatings.

The protector has an end view inner diameter slightly greater than or less than an outer cross-sectional diameter of the lead insulation. The protector can have any of the following forms: a helix (i.e., spring or coil, with the material used to make the helix possessing a cross-section of a polygon, circle, ellipse, oval, square, triangle, rectangle, or a semicircle), a mesh (i.e., woven or knitted, fabric or tube), or other Velcro or zipper-like interlocking mesh. A mesh design protector can be configured to be compressed lengthwise to increase the inner diameter of the end view of the protector so that it may be slipped over the insulation, where the protector upon being released would decrease its inner diameter back to its original inner diameter. A zipper design can have interlocking teeth.

The present invention can include a tool kit for positioning an abrasion resistant protector on an implantable lead, including a lead outer diameter sizing tool, i.e., a ring with slots of various outer diameters. The toolkit includes multiple, variably sized protectors for selection by a physician. The toolkit includes a tool configured to position the protectors on the implantable lead. The toolkit is intended to guide a physician in choosing a properly-sized protector and can be configured to modify the length of the protector.

Use of a protector reduces the risk of a scalpel cutting or nicking a soft silicone lead and prevents abrasion caused by contact with a pulse generator or other leads. A protector can be added to existing implanted leads or can be added to a new lead prior to placement or replacement.

A protector can be bonded to the outer diameter of the lead insulation. Alternatively, a protector can be fit into grooves previously made in (or molded into) the outer diameter of the lead insulation.

A protector can also be used for various other types of leads, such as, for example, neurostimulating, spinal cord, and muscle stimulating leads. A protector can also be used on various temporary leads to decrease the coefficient of friction (e.g., reduce friction against walls of the introducer typically used for vascular access during ultrasound, mapping, or ablation) and to protect against mechanical damage, including kinking.

A protector can be made in such a way as to hold a lead in a specific shape (e.g., to curl the lead around a pulse generator case).

Further features and advantages of the invention, as well as the structure and operation of various embodiments of the invention, are described in detail below with reference to the accompanying drawings.

BRIEF DESCRIPTION OF THE DRAWINGS

The foregoing and other features and advantages of the invention will be described with reference to the accompanying drawings. In the drawings, like reference numbers generally indicate identical, functionally similar, and/or structurally similar elements. Also in the figures, the left most digit of each reference number corresponds to the figure in which the reference number is first used.

FIG. 2 depicts a single conductor lead body having an insulation defect;

FIG. 3 depicts a pulse generator and transvenous lead system implanted transvenously in a patient;

DETAILED DESCRIPTION OF THE INVENTION

The preferred embodiment of the invention is discussed in detail below. While specific implementations are discussed, it should be understood that this is done for illustration purposes only. A person skilled in the relevant art will recognize that other components and configurations may be used without parting from the spirit and scope of the claimed invention.

Overview of the Invention

The present invention is directed to an abrasion and tear resistant protector disposed on a lead to prevent abrasion damage from frictional contact to the insulation of the lead. For example, the lead can be an implantable silicone lead.

The protector of the present invention can also be applied to a damaged area of the lead to prevent further damage to the insulation. The protector can be a flexible device that fits over the damaged area. The shape of the protector can be any of, for example, a simple coiled helix or spring, a more complex braided mesh or fabric shape, a solid tube design with or without axial support or a binder design. Where a simple helix, coil or spring shape design is employed, the end-view profile of the coil-forming strand can be circular, semi-circular, or of any other shape, such as, for example, a polygon (e.g., a triangle), and an ellipse.

The ends of the protector can be made smooth so as to prevent a sharp end of the protector from hooking into tissue or piercing the silicone insulation of the lead. A protector can be specially cut to a required length and still maintain a blunt end with no hooks to snag tissue.

To minimize friction between the protector and the pulse generator case, or other leads, the protector can be surface coated with a hydrophilic material.

The material used to make the protector can have the property of swelling when in contact with solvents permitting positioning the protector while swollen and allowing the protector to shrink into place. The solvents are preferably nonirritating, e.g., some materials such as, for example, hydrogels, can use water as the solvent. One embodiment uses heat-shrink technology to place the protector onto the lead.

The protector can be made of an elastomeric material to allow stretching over any larger diameter connector pins and seals at the proximal end of the lead. An embodiment of the invention constitutes a package of several sizes of protectors together from which a physician may select a particular protector. A sizing tool can be included in the package to facilitate placing the protector onto the lead in a quick and simple manner and to minimize the time and effort required by the physician.

The Invention

Figure 1A:
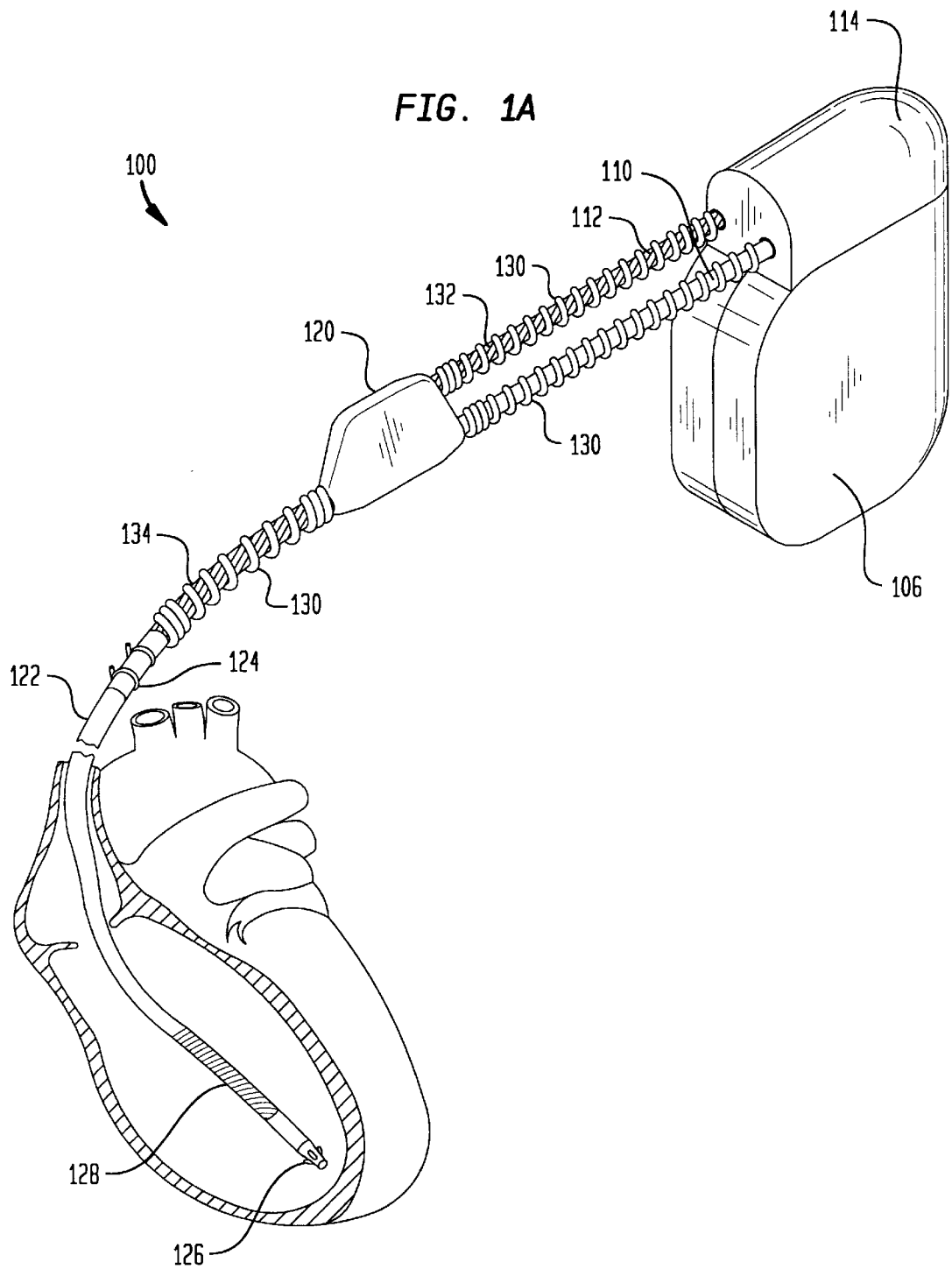
FIG. 1A depicts an ICD pulse generator case, and an exemplary helix-shaped lead protector embodiment placed on a two terminal, two leg implantable lead implanted transvenously in a patient's heart.

An implantable cardioverter defibrillator (ICD), also known as a pulse generator, monitors a patient's heartbeat and delivers electrical pulses through an implantable lead to the patient's heart to terminate episodes of ventricular tachyarrhythmias. FIG. 1A depicts a two terminal abrasion resistant implantable lead 100 implanted intravenously at one end, known as the distal end, in a patient and coupled at the other end, known as the proximal end, to a pulse generator 106, which is a pacemaker or ICD. Implantable lead 100 includes at the proximal end, two legs 110, 112 coupled to a header 114 of pulse generator 106 by connector pins (not pictured) through connector ports in header 114. The connector pins come in contact with terminals inside header 114. Legs 110, 112 are coupled to the lead body at yolk 120. Yolk 120, also commonly known as a lead body bifurcation, couples legs 110, 112 to lead body 122.

Figure 4A:
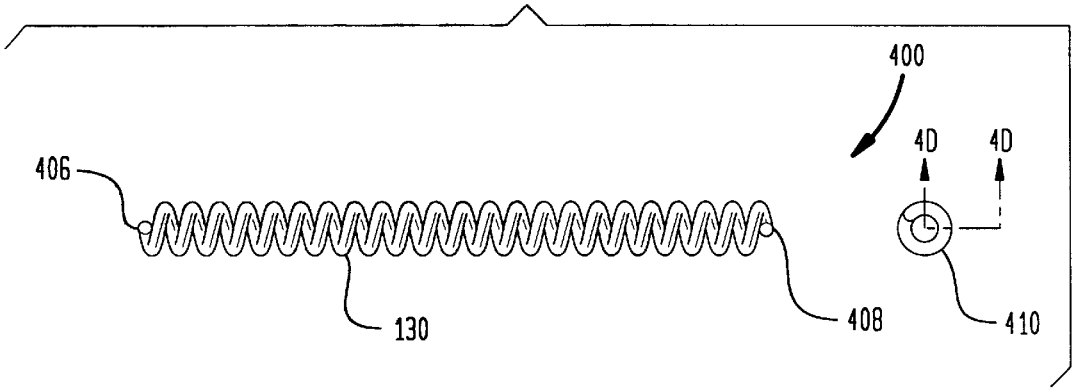
FIG. 4A depicts a side view and an end view of an exemplary embodiment of a helix-shaped protector.

Lead body 122 is implanted intravenously and is sutured where the lead enters the (usually subclavian or cephalic) vein. Lead body 122 includes a sense/pace tip electrode 126, having fixation tines shown, and a defibrillation electrode 128. A lead protector 130 is disposed on leg 110 of implantable lead 100. Lead protector 130 is an exemplary novel helix-shaped abrasion resistant device. Lead protector 130 can have its ends smoothed as depicted in FIG. 1A, and FIGS. 4A and 4C, below, to prevent damage to the silicone insulation of leg 110, for example. Lead protector 130 can also be placed on leg 112 at a leg protection site 132, on lead body 122 at a lead body protection site 134, or at any other sub-cutaneous portion of implantable lead 100 that could come in contact with the pulse generator case or be prone to scalpel nicks.

Figure 1B:
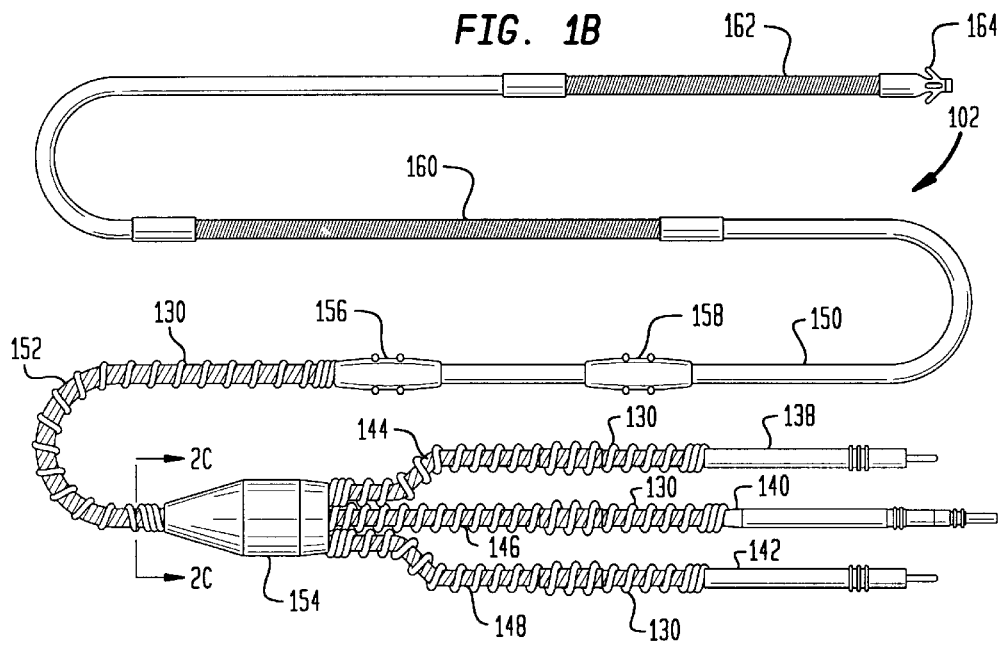
FIG. 1B depicts a protector placed on a three terminal, three leg implantable lead capable of being implanted transvenously in a patient.

FIG. 1B depicts a three terminal abrasion resistant implantable lead 102 having legs 138, 140, 142 with leg protection sites 144, 146, 148, respectively. Implantable lead 102 is also capable of being implanted transvenously in patient's heart. Implantable lead 102 includes a lead body 150 having a lead body protection site 152 located anywhere between a yolk 154 and up to suture sleeves 156, 158, also known as lead stabilizers. Implantable lead 102 also includes three electrodes 160, 162, 164.

Figure 1C:
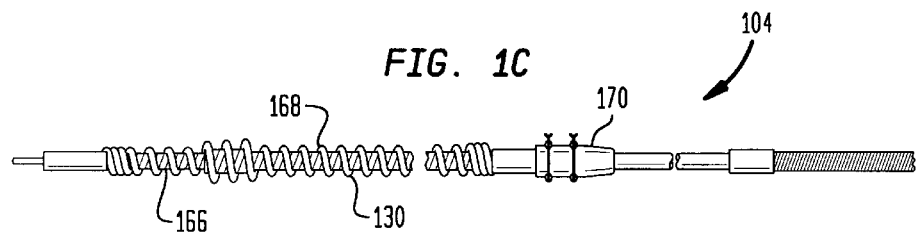
FIG. 1C depicts a single terminal, unipolar endocardial lead capable of being implanted transvenously in a patient with a protector.

FIG. 1C depicts a single terminal unipolar endocardial lead 104 capable of being implanted transvenously in a patient. Endocardial lead 104 includes a protection site 168 between the proximal end of the lead and a suture sleeve 170.

Protector 130 of the present invention can be used on other implantable leads, the three leads described are exemplary but not exhaustive.

Figure 1D:
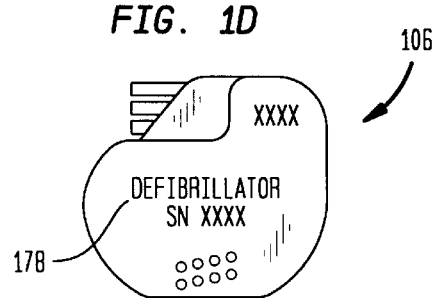
FIG. 1D depicts a side view of an exemplary implantable medical device or pulse generator.

FIG. 1D depicts a side view of a pulse generator 106 which can have a housing or can made of a material such as titanium with an etched engraving 178 such as a serial number or model number. The metallic surface of the can, when in frictional contact with implantable leads 100, 102, 104, can lead to abrasion induced insulation defects.

Leg 112 of implantable lead 100 is an example of a conventional lead leg containing one or more conductors surrounded by a flexible insulating material such as silicone which is susceptible to such defects.

During extraction and replacement of pulse generator 106 for battery depletion or other reason such as ICD upgrade, a physician will conventionally examine the proximal end of lead body 122 and legs 110, 112 for any visible insulation defects or conductor fractures. Defects can occur, for example, by frictional contact between the pulse generator 106 and the insulation 204 of leg 112. Insulation defects often occur at legs 110, 112 and lead body 122 because of their proximity to pulse generator 106.

FIG. 2 depicts an insulation defect or lead fracture in a single conductor lead 200, also known as a unipolar lead, having an abrasion 206 in insulation 204 of a single conductor lead leg, such as leg 112 of three terminal implantable lead 100. Abrasion 206 exposes conductor 202 to a possible short circuit to the surrounding tissue of the patient.

Physicians could attempt to patch the site of an insulation defect by applying to the site of the insulation defect, a room temperature vulcanization material (RTV) such as SILASTIC®, Medical Adhesive Silicone Type A from DOW CORNING. An improved technique for patching a lead requires that a physician apply RTV material to the insulation defect followed by placing a protector 130 over the location of the insulation defect. Whether a physician can attempt a repair depends on the site of the insulation defect.

FIG. 3 illustrates a review of sites of potential insulation defects 302 depicting a pulse generator 106 and an implantable bifurcated lead 104 implanted transvenously in a patient. Insulation defects can occur, for example, at lead leg 166 at a location 312 by contact with the can, and 314 outside the vein by contact between leads. The protector 130 of the present invention is designed for use at any subcutaneous location, including at least locations 312, and 314 facilitating at least prevention of insulation defects and fractures at additional locations than conventionally possible.

The Protector

FIG. 4A includes a side view and an end view of a helix-shaped protector 400, also referred to as a "spring", depicting an exemplary embodiment of protector 130 of the present invention having ends 406, 408 and circular end view 410. The side view of FIG. 4A is merely an example embodiment of protector 130, other embodiments include a tighter helix, a looser helix, and a helix of varying pitch. Alternatively, protector 130 can have an end-view of another shape. An exemplary but non-exhaustive list of other end-views include an ellipse, oval, semicircle, square, rectangle, triangle, polygon or other shape.

Figure 4B:
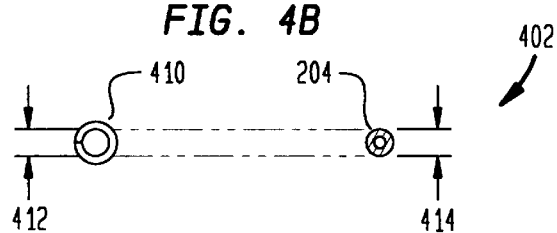
FIG. 4B depicts end views of an exemplary helix-shaped protector and a lead insulator to illustrate their relative diameters.
Figure 4C:
FIG. 4C depicts an exemplary smoothed end of the protector.
Figure 4D:
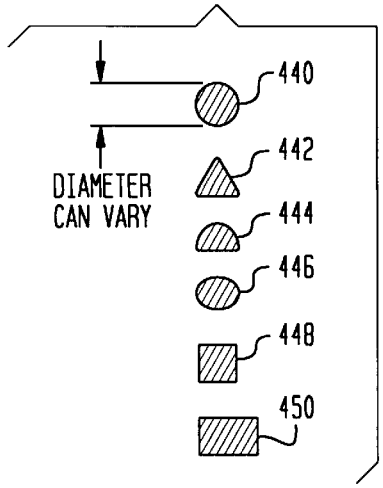
FIG. 4D depicts exemplary cross-sections of the material of the protector.

The material of protector 130 has a circular cross-section (see circular cross-section 440 in FIG. 4D). Preferably, the material of protector 130 has a cross-sectional diameter of between 3–30 mils. Alternatively, the material of protector 130 can have a cross-section of another shape. Alternatively, the diameters of circular cross-section 440 can vary. An exemplary but non-exhaustive list of other cross-sections include an ellipse, oval, semicircle, square, rectangle, triangle, polygon or other shape. FIG. 4D depicts alternate exemplary cross-sections 440–450 of the material of lead 130.

FIG. 4B depicts an end view of a protector and lead insulation illustrating relative diameters of a circular end view 410 of protector 130, and a circular cross-section of insulation 204 of leg 110, 112 or lead body 122. Circular end view 410 of protector 130 has an inner diameter 412. Circular cross-section of insulation 204 has an outer diameter 414 which is approximately equal to inner diameter 412 of protector 130 to ensure a snug fit. Outer diameter 414 can be slightly larger than or slightly smaller than inner diameter 412, to permit a looser or tighter fit. In one embodiment, pitch and or the angle of the loops of the helix can vary. In another embodiment, the diameter of the end view and also the cross sectional area can vary. A kit can be supplied to a physician including protectors 130 of varying diameters and an outer diameter sizing tool for selection of the properly sized protector 130. The protector 130 of preferable choice is one that has a so called "line fit," or a slightly smaller inner diameter 412 than outer diameter 414 of insulation 204 of the lead so that it fits snugly against outer diameter 414.

An embodiment uses heat-shrink technology to place the protector onto the lead. The material used to manufacture the protector can incorporate shape memory to be able to shrink snugly onto the lead body. The protector preferably exerts minimal force on the lead insulation to prevent any compression failure of the lead. The protector preferably has a "snug" fit in order to minimize tissue "ingrowth" or attachment.

FIG. 4C depicts an exemplary smoothed end of protector 130. A protector can be cut to a desired length and still maintain a blunt end with no hooks to snag tissue.

Protector 130 can be designed to be applied and removed easily. The protector can be made of an elastomeric material to allow stretching over any larger diameter connecting pins and seals at the proximal end of the lead. A tool can be provided to the physician for easily adding and removing protector 130 to and from the lead. A tool kit for positioning protector 130 can accompany protector 130. The toolkit can include a tool configured to position the protectors on the implantable lead. The toolkit can also include a lead outer diameter sizing tool, i.e., a ring with slots of various outer diameters disposed thereon. The toolkit can also include multiple, variably sized protectors for selection by a physician. The toolkit is intended to guide a physician in choosing a properly-sized protector 130 and can be configured to modify the length of protector 130.

Protector 130 can be fabricated from a flexible, elastomeric, biocompatible material such as, for example, a thermoset or thermoplastic homopolymer, a blend of polymers, a coated polymer, or a filled polymer. Specific polymers appropriate include, for example, polytetrafluoroethylene (PTFE), polyurethanes, polycarbonate polyurethanes, polyolefins, polyesters, or other known polymers with an acceptable history of long-term implant use.

The material used to make protector 130 can have the property of swelling when in contact with solvents permitting positioning the protector while swollen and allowing the protector to shrink into place.

Since eventually any material, including metals, may show signs of wear when under conditions of continuous abrasion, protector 130 should not be made of a hardness that could damage the wall of a case of a defibrillator or pacing pulse generator 106. An embodiment of the protector has a hydrophilic surface to minimize the coefficient of friction between the pulse generator and the leads. The hydrophilic surface coating can also include heparin or other antithrombogenic coatings. Hydrogels such as poly (hydroxyethyl methacrylate) (PHEMA), poly (hydroxyethacrylate) (PHEEMA), poly (hydroxydiethoxyethyl methacrylate) (PHDEEMA), poly (methoxyethyl methacrylate) (PMEMA), poly (methoxyethoxyethyl methacrylate) (PMEEMA), poly (methoxydiethoxyethyl methacrylate) (PMDEEMA), poly (ethylene glycol dimethacrylate) (PEGDMA), poly(vinyl alcohol) (PVA), poly(ethylene oxide) (PEO), poly (carboxylic acids), poly(acrylic acid) (PAA), poly (methacrylic acid) (PMAA), poly(N-vinyl-2-pyrollidone) (PNVP), poly(acrylonitrile) (PAN), cellulose ethers, and water-soluble cellulosic polymers can make acceptable hydrophilic coatings.

A coating can be applied to protector 130 in various ways including the use of UV Radiation, Ionizing Radiation, and Plasma Discharge.

Figure 5A:
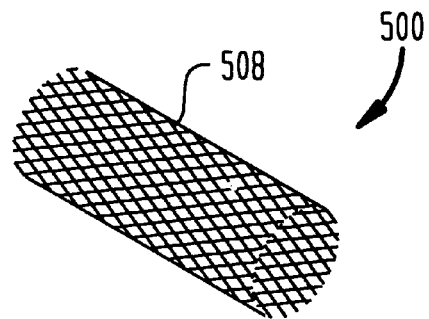
FIG. 5A depicts exemplary mesh or fabric embodiments of the protector.

Protector 130 can be made of various other shapes and materials other than a continuous helix to facilitate easy application and removal to and from the lead while still imparting flexibility. FIG. 5A depicts exemplary mesh, fabric, or fiber embodiments 500 of protector 130. A mesh or fabric tube 508 embodiment of protector 130 can be used. Mesh or fabric tube 508 can be made of a woven material such as mesh or a tubular knitted polyester mesh.

An embodiment of the protector having a mesh design can be compressed lengthwise to increase the inner diameter of the protector permitting it to be slipped over the lead, and upon release the protector would shrink back to its original inner diameter and gently snug the silicone outer diameter, analogous to a children's toy known as "chinese handcuffs."

Figure 5B:
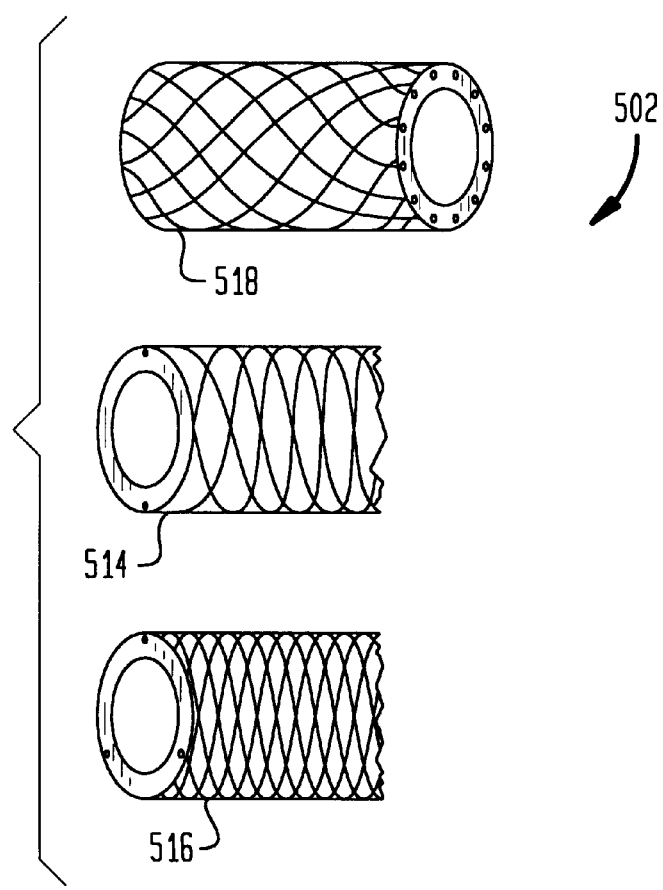
FIG. 5B depicts axial, biaxial, triaxial and multi-axial reinforced embodiments of the protector.

Protector 130 can be made of a simple tube or a tube with an embedded fiber reinforcement. FIG. 5B depicts exemplary biaxial 514, triaxial 514 and n-axial 518 embodiments. Protector 130 could be placed over legs 110, 112, for example, from the proximal end of the lead. Protector 130 could be made of a stretchable material to permit stretching over the connectors at the proximal end. Alternatively, protector 130 could be placed on the lead by a manufacturer.

Figure 5C:
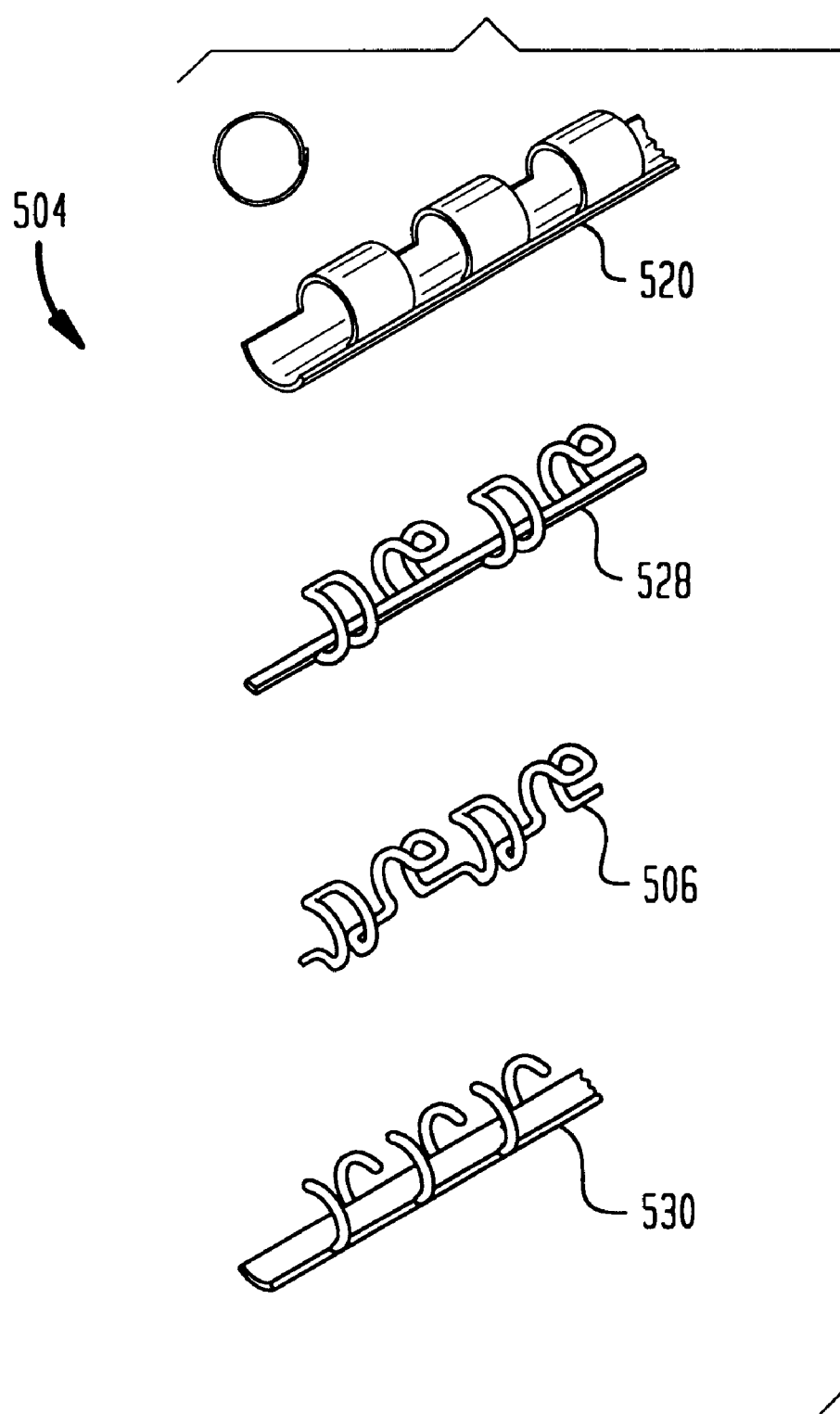
FIG. 5C depicts binder type embodiments of the protector.

FIG. 5C depicts an exemplary binder type embodiment 520. Examples of other binder embodiments of protector 130, include an alternating loop 528 with a spine, an alternating loop 506 without a spine, and an alternating hook 530. Alternating hook 530 can have rounded ends similar to the ends of protector 130 depicted in FIG. 4C. Binder embodiments 504 are more easily applied and removed than a helix-shaped protector 130 and can be easily applied to a lead that is already implanted in a patient's heart. Binder embodiments 504 of other shapes can be made according to the present invention as would be apparent to one skilled in the relevant art.

Figure 6A:
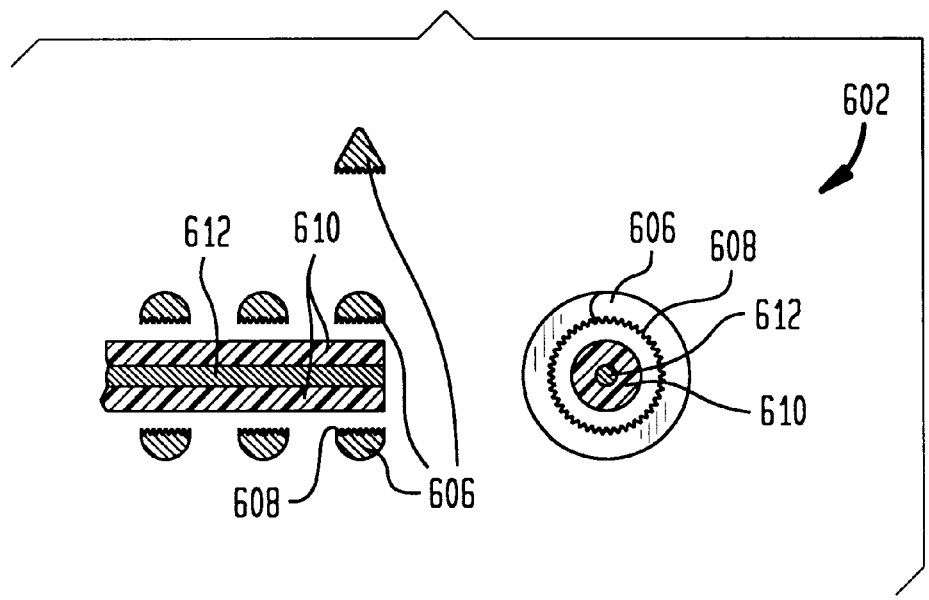
FIG. 6A depicts side, cross-sections, and end views of a protector having a textured inner edge for gripping the insulation of a lead.

The inner surface of the protector can have a frictional texture so as to grip the outer surface of the lead insulation. FIG. 6A depicts side, cross-sectional, and end views of a textured grip protector 602 including protector 606 having textured inner surface 608 for gripping insulation 610 which surrounds conductor 612.

Figure 6B:
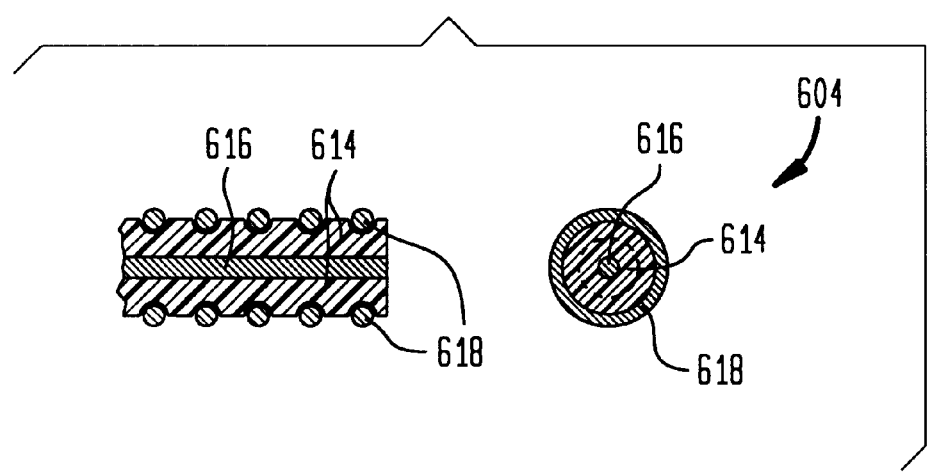
FIG. 6B depicts side and cross-sectional views of an improved implantable lead having a grooved outer insulation surface for receiving a protector.

An improved implantable lead having premolded grooves in the outer surface of the silicone insulation of the lead can be formed, into which a protector can be placed. FIG. 6B depicts side, cross-sectional, and end views of an improved implantable lead 604 including a grooved insulation 614 surrounding a conductor 616, into which protector 618 is placed. Alternatively, a protector 130 can be bonded to the insulation of a lead. Alternatively, protector 130 can be applied by manufacturers to a lead.

Using protector 130 reduces the risk of a scalpel cutting or nicking a soft silicone lead and prevents abrasion caused by contact between different portions of a lead and between a lead and a pulse generator. Protector 130 can also be added to existing implanted leads or can be added to a new lead prior to placement or replacement.

Protector 130 can also be used on various other types of leads. For example, protector 130 can also be applied to drug stimulating, neurostimulating, spinal cord, and muscle stimulating leads. Protector 130 can also be used on temporary leads to decrease the coefficient of friction (e.g., ultrasound, mapping, ablation) and to protect against mechanical damage, including kinking.

Protector 130 can be made in such a way as to hold a lead in a specific shape (e.g., to curl the lead around a pulse generator case).

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. An abrasion resistant device for use on an implantable lead having insulation, said device comprising:

a protector disposed about a portion of the insulation, said protector having an inner end-view diameter equal to or less than an outer diameter of the cross-section of the insulation and being configured to substantially prevent abrasion of the insulation by separating the insulation from contact with a generator case.

2. The device of claim 1, wherein said protector is made from a flexible, elastomeric material.

3. The device of claim 2, wherein said flexible, elastomeric material comprises a biocompatible material selected from one of the following: thermoset or thermoplastic homopolymer, a blend of polymers, a coated polymer, a filled polymer.

4. The device of claim 3, wherein said polymer comprises a polymer selected from one of the following: polytetrafluoroethylene (PTFE), polyurethanes, polycarbonate polyurethanes, polyolefins, polyesters, and other known polymers acceptable for implant use.

5. The device of claim 1, wherein said protector comprises a hydrophilic surface coating to minimize the coefficient of friction between said protector and said generator case.

6. The device of claim 5, wherein said hydrophilic surface coating comprises a material selected from one of the following: heparin, other antithrombogenic coatings, and hydrogels.

7. The device of claim 6, wherein said hydrogel material comprises a material selected from one of the following: poly(hydroxyethyl methacrylate) (PHEMA), poly(hydroxyethacrylate) (PHEEMA), poly(hydroxydiethoxyethyl methacrylate) (PHDEEMA), poly(methoxyethyl methacrylate) (PMEMA), poly(methoxyethoxyethyl methacrylate) (PMEEMA), poly(methoxydiethoxyethyl methacrylate) (PMDEEMA), poly(ethylene glycol dimethacrylate) (PEGDMA), poly(vinyl alcohol) (PVA), poly(ethylene oxide) (PEO), poly(carboxylic acids), poly(acrylic acid) (PAA), poly(methacrylic acid) (PMAA), poly(N-vinyl-2-pyrollidone) (PNVP), poly(acrylonitrile) (PAN), cellulose ethers, and water-soluble cellulosic polymers.

8. The device of claim 1, wherein said protector has an end view with one of the following shapes: polygon, circle, oval, square, triangle, rectangle, and a semicircle; and is constructed of a material having a cross-section with one of the following shapes: polygon, circle, oval, square, triangle, rectangle, and a semicircle.

9. The device of claim 8, wherein said cross-section of said material of said protector has a diameter between 3 and 30 mils.

10. The device of claim 1, wherein said protector has a mesh design that may be compressed lengthwise to increase the inner end-view diameter of said protector so that it may be slipped over the insulation, wherein said mesh upon being released can shrink to a close fit with the insulation.

11. The device of claim 1, wherein said protector has a binder design comprising interlocking spaced tabs.

12. The device of claim 1, wherein said protector has a zipper design comprising interlocking teeth.

13. An abrasion resistant device for use on an implantable lead having insulation, said device comprising:

a protector having a helix configuration disposed about a portion of the insulation, said protector substantially preventing abrasion of the insulation by separating the insulation from contact with a generator case.

14. The device of claim 1, wherein said protector comprises first and second ends, said first and second ends being bonded to said protector.

15. An abrasion resistant implantable lead system comprising:

a lead having a grooved outer surface; and a protector disposed about said lead and received by said grooved outer surface.

16. An abrasion resistant implantable lead system comprising:

a lead and a protector disposed about said lead wherein said protector has a frictional inner texture to grip said lead.

* * * * *